(12) United States Patent
Noras (10) Patent No.: US 9,936,894 B2
(45) Date of Patent: Apr. 10, 2018

(54) RECTAL COIL FOR MAGNETIC-RESONANCE TOMOGRAPHY

(71) Applicant: Hubert Noras, Würzburg (DE)

(72) Inventor: Hubert Noras, Würzburg (DE)

( * ) Notice: Subject to any disclaimer, the term of this patent is extended or adjusted under 35 U.S.C. 154(b) by 95 days.

(21) Appl. No.: 14/652,677

(22) PCT Filed: Sep. 1, 2014

(86) PCT No.: PCT/DE2014/100313
§ 371 (c)(1),
(2) Date: Jun. 16, 2015

(87) PCT Pub. No.: WO2015/032386
PCT Pub. Date: Mar. 12, 2015

(65) Prior Publication Data
US 2015/0323621 A1    Nov. 12, 2015

(30) Foreign Application Priority Data

Sep. 4, 2013   (DE) .......................... 10 2013 109 660

(51) Int. Cl.
*A61B 5/055* (2006.01)
*A61B 17/34* (2006.01)
(Continued)

(52) U.S. Cl.
CPC ............ *A61B 5/055* (2013.01); *A61B 5/4381* (2013.01); *A61B 5/6873* (2013.01); *A61B 17/3403* (2013.01); *G01R 33/34084* (2013.01); *A61B 5/0555* (2013.01); *A61B 5/6853* (2013.01); *A61B 10/0241* (2013.01);
(Continued)

(58) Field of Classification Search
CPC ............ A61B 10/0241; A61B 17/3403; A61B 2017/3405; A61B 2017/3452; A61B 2560/0285; A61B 5/055; A61B 5/0555; A61B 5/4381; A61B 5/6853; A61B 5/6873; G01R 33/34007; G01R 33/34084
See application file for complete search history.

(56) References Cited

U.S. PATENT DOCUMENTS 4,557,260 A * 12/1985 Reyes, Jr. .............. A61B 17/42
                                                               5/648
5,050,607 A *  9/1991 Bradley ................ A61B 1/307
                                                              600/423
(Continued)

FOREIGN PATENT DOCUMENTS

JP          S62286451 A     12/1987

OTHER PUBLICATIONS

International Search Report (ISR) with regard to PCT/DE2014/100313 as completed by the EPO on Jan. 19, 2015 and dated Jan. 28, 2015.

*Primary Examiner* — Ruth S Smith
(74) *Attorney, Agent, or Firm* — Westman, Champlin & Koehler, P.A.

(57) ABSTRACT

The invention concerns a rectal coil for magnetic resonance tomography, with a coil for transmitting and/or receiving magnetic resonance tomography electromagnetic signals, an inflatable balloon for securing or positioning the coil in the intestine and a shaft by means of which the coil and balloon are connected and which is used to introduce the rectal coil into the rectum, the coil being attached outside the balloon.

9 Claims, 6 Drawing Sheets (51) Int. Cl.
   *G01R 33/34*   (2006.01)
   *A61B 5/00*    (2006.01)
   *A61B 10/02*   (2006.01)

(52) U.S. Cl.
   CPC ........... *A61B 2017/3405* (2013.01); *A61B 2017/3452* (2013.01); *A61B 2560/0285* (2013.01); *G01R 33/34007* (2013.01)

(56) References Cited

U.S. PATENT DOCUMENTS

| | | | |
|---|---|---|---|
| 5,307,814 A |  | 5/1994 | Kressel |
| 5,365,928 A |  | 11/1994 | Rhinehart et al. |
| 5,451,232 A | * | 9/1995 | Rhinehart ............ A61B 5/055 600/421 |
| 6,263,229 B1 | * | 7/2001 | Atalar ............ G01R 33/34007 324/318 |
| 7,912,531 B1 | * | 3/2011 | Chiu ............ A61B 5/055 324/309 |
| 2002/0101241 A1 |  | 8/2002 | Chui |
| 2008/0009673 A1 | * | 1/2008 | Khachi ............ A61B 1/00082 600/116 |
| 2009/0082664 A1 |  | 3/2009 | Schilling |
| 2010/0010471 A1 | * | 1/2010 | Ladd ............ A61M 31/007 604/514 |

\* cited by examiner

RECTAL COIL FOR MAGNETIC-RESONANCE TOMOGRAPHY

The invention relates to a rectal coil for magnetic-resonance tomography and a related method for the use thereof.

In imaging magnetic-resonance tomography, rectal coils are already used to permit imaging, particularly of the prostate, and to increase the resolution. In the context of the invention, the term "rectal coil" means a device that possesses at least one electrical coil, which is fastened on a shaft and can thereby be pushed into the rectum. This electrical coil comprises the electromagnetic signals of magnetic-resonance tomography. In order to extend the rectum as little as possible, the electrical coil, abbreviated to "coil" hereinafter, is pushed in the radially compressed state through the rectum and expanded to the necessary cross-section within the intestine with the aid of a balloon, which is known from German patent DE102007046169A1 and U.S. Pat. No. 5,365,928. According to this prior art, however, the coil is located within the balloon and is thereby spaced from the prostate. Furthermore, the coil is aligned relatively arbitrarily as the balloon is pumped up.

The object of the invention is to further improve the quality of imaging of the prostate with the aid of MRT processes. The goal is not only to make the coil area as large as possible but to orient a plane of symmetry of the coil generally in the plane of symmetry of the body.

To achieve this object, the invention proposes that the coil is applied outside the balloon.

The entire rectal coil usually includes, as coil, a quadrature or multichannel coil and is pushed through the intestine into the appropriate position, that is to say as far as the prostate. The manner of fastening the coil on the balloon is achieved by means of a suitable structural design of the rectal coil.

An advantageous possibility of concretization is to use a flexible half-tube. In the stationary state, it possesses a small cross-section and permits the rectal coil to be introduced into the rectum without the closing muscle being excessively extended. By the bending open, spreading or opening of this half-tube, the coil can be positioned in the intestine and fixed in the intestine by means of a holding device or a balloon (with or without liquid). The coil itself is accommodated on the half-tube on the outside or on the inside or preferably in the wall. The coil is easily oriented with the aid of the balloon in the direction of the prostate, so that no pressure can be exerted on the prostate and it nevertheless lies very close against the intestine wall in the direction of the prostate. But the exertion of pressure on the prostate also occasionally proves advantageous, since, in this manner, a fixing of the prostate also takes place and is maintained when the patient moves slightly and changes, for example, the leg position. The conventional coil known from the prior art develops in the interior of the balloon, principally approximately in the centre. The balloon serves as a carrier of the conventional coil and bears against the intestine at all sides. In our solution, on the other hand, the coil is located outside the balloon. Since the coil is attached on a flexible circuit board and is bent open with the half tube, the receiver antenna size is always of equal size, since for a given inflation volume of the balloon, the effective surface area of the coil is clearly determined. In the bent-open state, the maximum parallel projectable surface area of the half-tube, and therefore the effective surface area of the coil, is much greater than in the stationary state. This circumstance greatly improves the image quality of magnetic-resonance tomography.

It is expedient to cast, inject or bond the flexible circuit board with the coil into this half-tube during the manufacture of the half-tube, which is designed such that it flexible, so that it is well protected in the wall of the half-tube and the tensile loading of the coil is minimum during bending open of the half-tube. Alternatively to this, the coil can be attached on the inside of the half-tube, which simplifies the manufacture of the half-tubes or attached on the outside of the half tubes, wherein it can be positioned as close as possible to the prostate. The connection wires of the coil are guided outwardly from the half-tube through a shaft. In the resting state, the entire rectal coil is rolled up about the longitudinal axis for introduction, then pushed through the closing muscle and into the suitable position in the intestine. Here, it is bent open with the aid of the balloon and unfolded.

In one embodiment, the coil is intended for one-off use, which on one hand is more hygienic and on the other hand to not place high requirements on the quality of the material and the design, since the bending open of the coil usually only takes place one. The permanent use of the rectal coil, with the replacement of a balloon intended for one-off use, is a further interesting embodiment, because the balloon cannot be autoclaved, through the rest of the rectal coil can.

A further variant is to equip the rectal coil with a balloon having multiple chambers. It is of advantage here that the coil can be oriented in a more targeted way by means of different inflation of the chambers with air, gel or a liquid. Inflation with a liquid, compared to pressurization with air or a gas, has the advantage that fewer artifacts occur.

In a multi-chamber system, it proves advantageous if the individual chambers extend parallel to one another and run in the longitudinal direction, that is to say are spaced from one another in the azimuth. The embodiment permits, by individual inflating of the individual chambers with different pressure, a rotation of the coil, in the introduced state, about the azimuth. In the prior art, it is necessary to rotate the entire device about the longitudinal axis of the shaft, which does not permit a precise orientation and adjustment. The multi-chamber system permits the coil to be oriented in a precise manner onto the target object, in this case the prostate.

For application of the coil, a flexible circuit board can be used.

To improve the resolution, a plurality of coils can be used in the rectal coil.

As a result, the invention offers the following advantages compared to the prior art:
  The coil is brought closer to the prostate, which improves the resolution.
  At the same time, the effective surface area of the coil becomes as large as possible.
  Furthermore, in particular with the use of a plurality of balloons, the spatial orientation of the coil can be controlled better.

In a particular embodiment, further devices, for example for needle guidance, are attached between the balloon and coil to permit a biopsy that is as accurate as possible locally.

Further details and features of the invention are explained below in greater detail with reference to an example. However, this is not intended to limit the invention but only explain it. In schematic, view.

Figure 1:
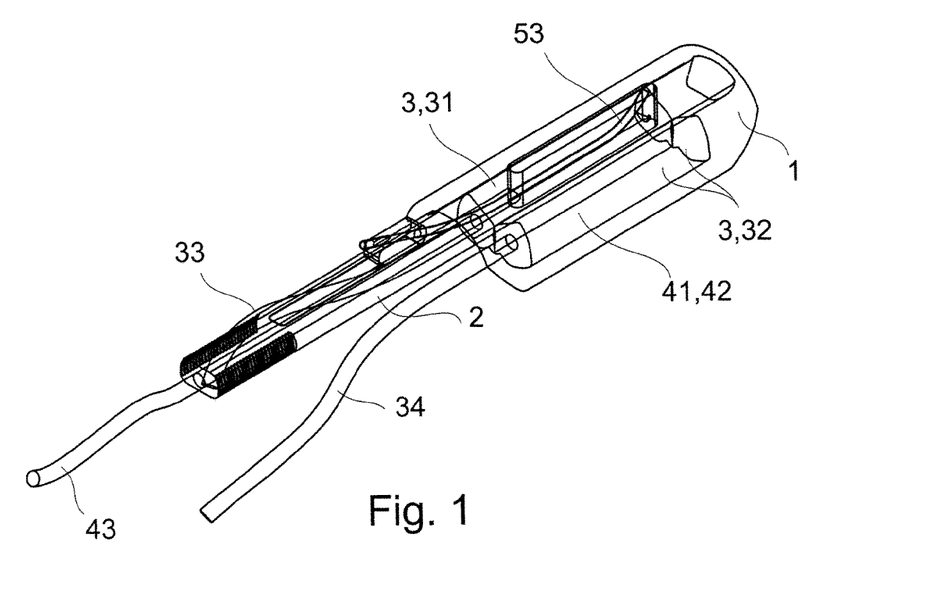
FIG. 1 shows the rectal coil in overall view in the resting state
Figure 10:
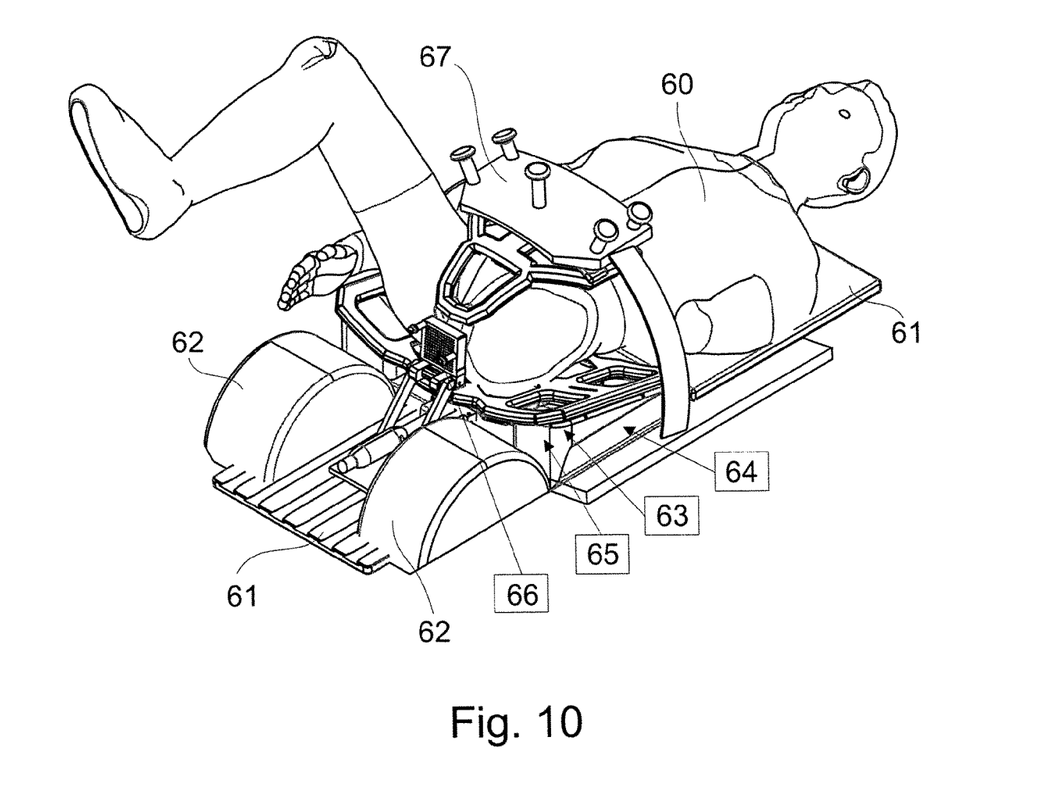

FIG. 10 Examination set-up with base plate, patient, coil construction, and wedge pillow FIG. 1 shows the rectal coil in overall view in the resting state. A half-tube 1 is attached on its inner side longitudinally and centrally on a shaft 2, with which the rectal coil can be guided and fixed externally to the patient. The term half-tube is not to be taken strictly literally, since in the resting state, the cross-section of the half-tube 1, which is circular in form, is preferably somewhat more than a semi-circle. A balloon 3 is connected to the half tube 1 on its inner side and thereby covers the shaft 2. Preferably the balloon 3 is subdivided into a plurality of balloon chambers 31, 32. The use of a plurality of balloon chambers 31, 32 offers, compared to the use of a balloon 3 consisting of only one balloon chamber, the advantage that, due to the, as appropriate, non-equal filling of the balloon chambers 31, 32, the rectal coil can be much better oriented on the intestine wall. Two balloon chambers 31, 32 are a good number, but even more balloon chambers can also be inserted, at the head, that is to say distant from the stem of the shaft 2, and at the base, where the shaft 2 leaves the half-tube 1, which can further facilitate the positioning of the rectal coil. The balloon chambers 31, 32 can be individually filled by means of tubes 33, 34. The aforementioned and further components of the rectal coil can also be seen in FIG. 2, which shows a cross-section of the rectal coil in the resting state from the point of view of the doctor, that is to say in the direction of the rectum.

Figure 2:
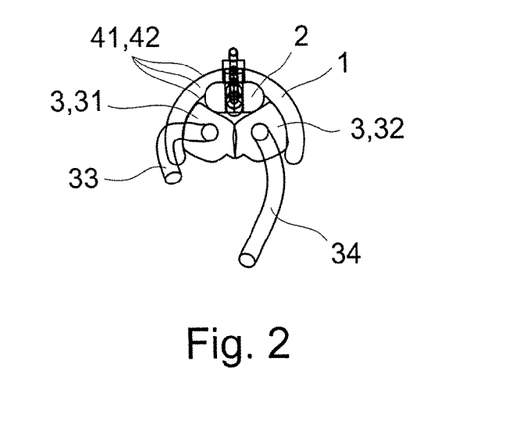
FIG. 2 shows a cross-section through the rectal coil in the resting state

In the wall of the half-tube 1, approximately at the location of its central radius, surrounded by material of the half-tube 1, at least one coil 41, 42 is introduced. The coil 41, 42 is preferably realized in advanced in a flexible circuit board. In the subsequent manufacture of the half-tube 1 by injection molding, wherein the form of the half-tube 1 in the resting state is defined, the coil, 41, 42, can be cast and fixed approximately centrally between the inside and outside of the half-tube 1, for example by feeding the injection material through a plurality of nozzles in each case, from both sides of the flexible circuit board. The flexible circuit board can be equally well pressed at the edge between two half-shells of the injection mold, the overhanging edges of the flexible circuit board being cut off after injection molding. As an alternative to this, the injection molding of the inner side of the half-tube 1, the flexible circuit board with the coil 41, 42 forming the outer wall, and subsequently the outer portion of the half-tube 1, the inner portion of the half-tube 1, with the flexible circuit board already applied, forming the inner wall, in an expedient manner in two operations. Alternatively to the introduction of the coil 41, 42 in the wall of the half-tube 1, the coil 41, 42 can also be applied on the inside or on the outside of the half-tube 1. For application or assembly, bonding is also suitable in these cases. The connection wires of the coils 41, 42 are guided outwardly from the half-tube through the shaft 2 in a cable 43.

Figure 3:
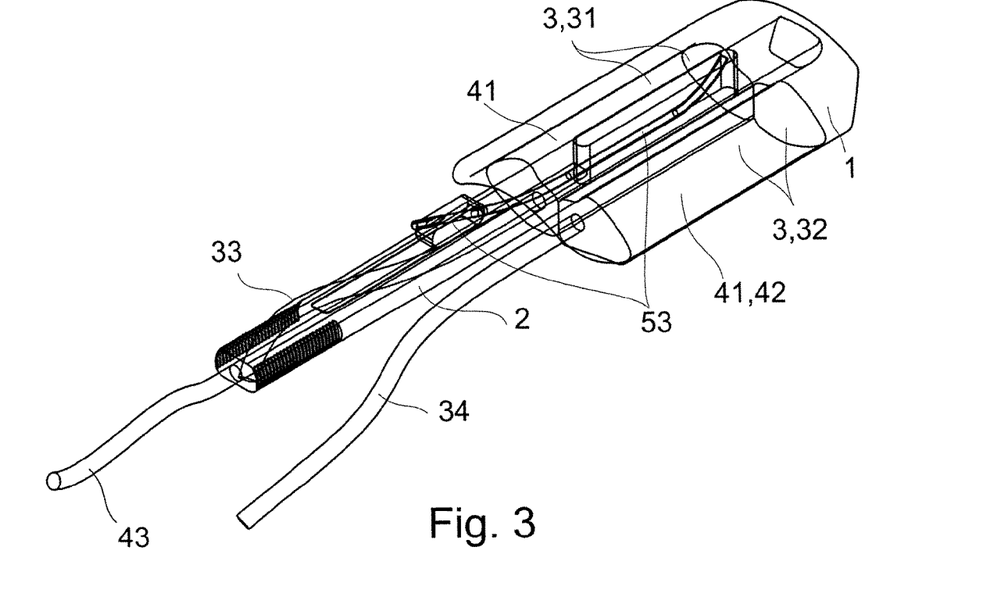
FIG. 3 shows the rectal coil in the bent-open state in overall view
Figure 4:
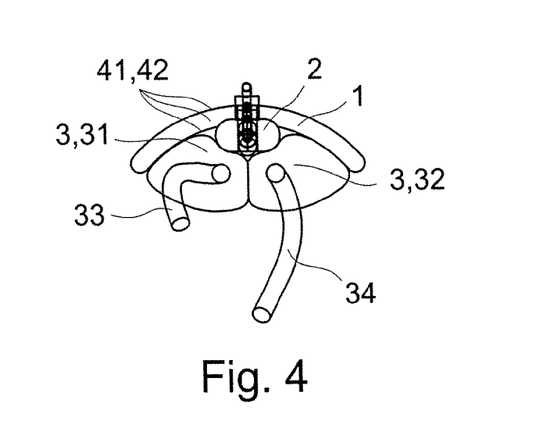
FIG. 4 shows a cross-section through the rectal coil in the bent-open state
Figure 5:
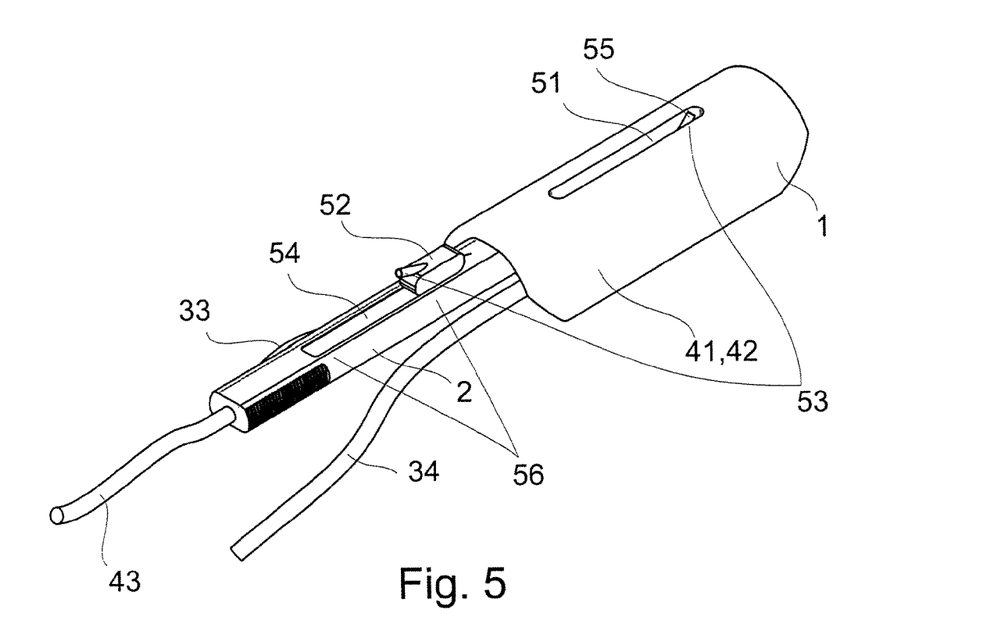
FIG. 5 shows the rectal coil in overall view in the resting state
Figure 6:
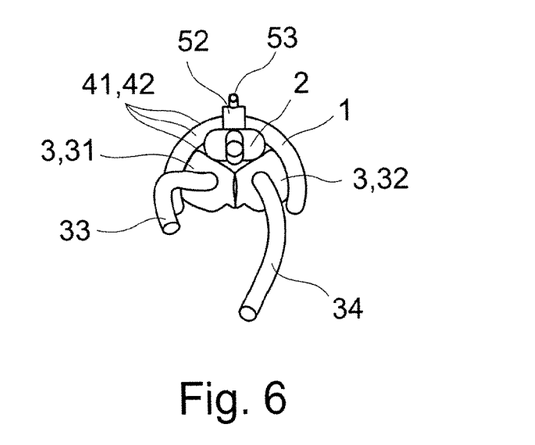
FIG. 6 shows a cross-section through the rectal coil in the resting state
Figure 7:
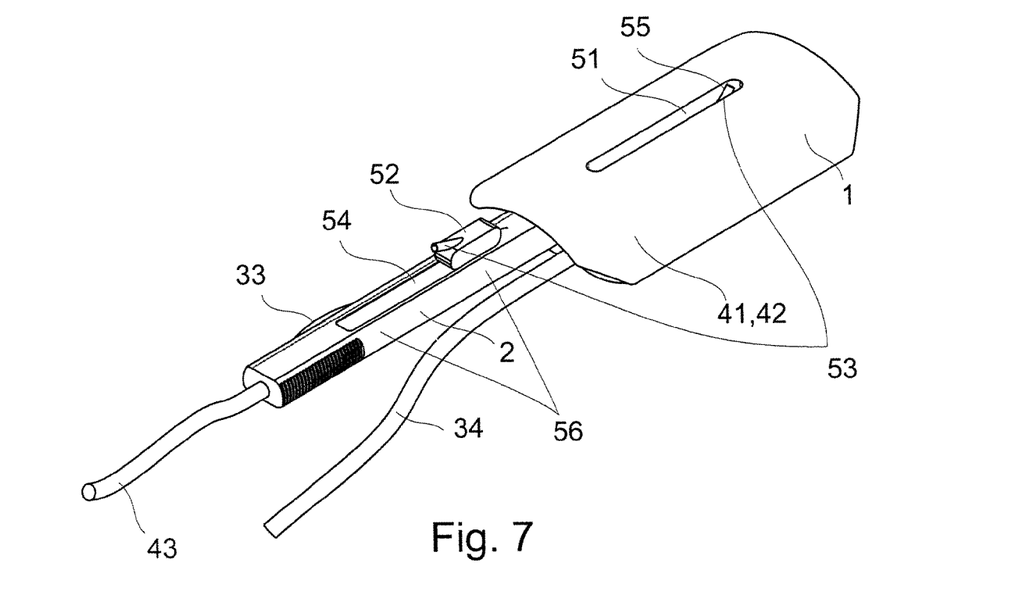
FIG. 7 shows the rectal coil in the bent-open state in overall view
Figure 8:
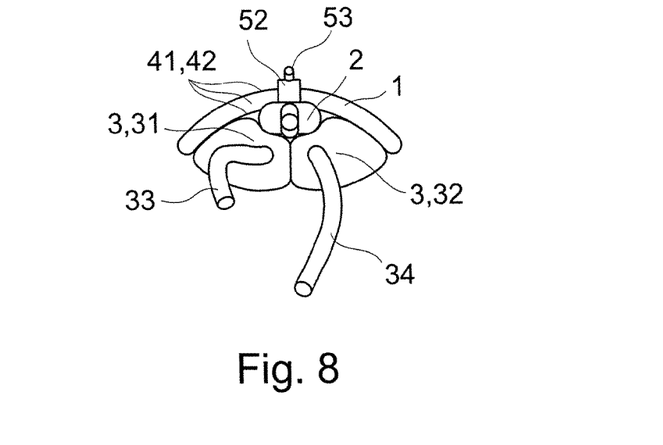
FIG. 8 shows a cross-section through the rectal coil in the bent-open state

The half-tube 1 is so flexible that it can be bent open and enlarged in cross-section by filling the balloon 3 or the balloon chambers 31, 32. To this end, the balloon chambers 31, 32 are individually filled with air or with a non-imaging liquid via the associated tubes 33, 34 The state achieved thereby can be seen in FIG. 3 and FIG. 4. These correspond to FIG. 1 and FIG. 2 respectively, but with the half-tube 1 and rectal coil in the bent-open state instead of in the resting state. The cross-sections of the balloon 3 and the balloon chambers 31, 32 are extended in the bent open state. The cross-section of the half-tube 1 now preferably comprises a quarter-circle, but with a larger diameter than in the resting state. Those outer walls of the balloon 3 that are not adjacent to the half-tube 1 are, when the half-tube 1 and rectal coil are in the bent-open state, pressed away from the half-tube 1 and, in their contour, can also approximately produce a quarter-circle. In result, the extended cross-section of the rectal coil fixes the latter in the intestine. The coils 41, 42, of which the form follows the form of the half-tube 1, are pressed close to or directly onto the intestinal wall and are thereby located very close to the prostate. The balloon 3 is preferably only filled to the extent that the prostate is not yet compressed.

It is conceivable to produce the shaft 2 and other components of the rectal coil, for example the half-tube 1, as a single component of the rectal coil. With the inclusion of this and similar constructions, the shaft 2 is that elongated and adequately stiff portion of the rectal coil on which the rectal coil can be held and introduced through the rectum.

FIGS. 5, 6, 7 and 8 show the rectal coil according to the invention, as in FIGS. 1, 2, 3 and 4 respectively, but not transparent, without auxiliary lines for non-visible components.

Figure 9:
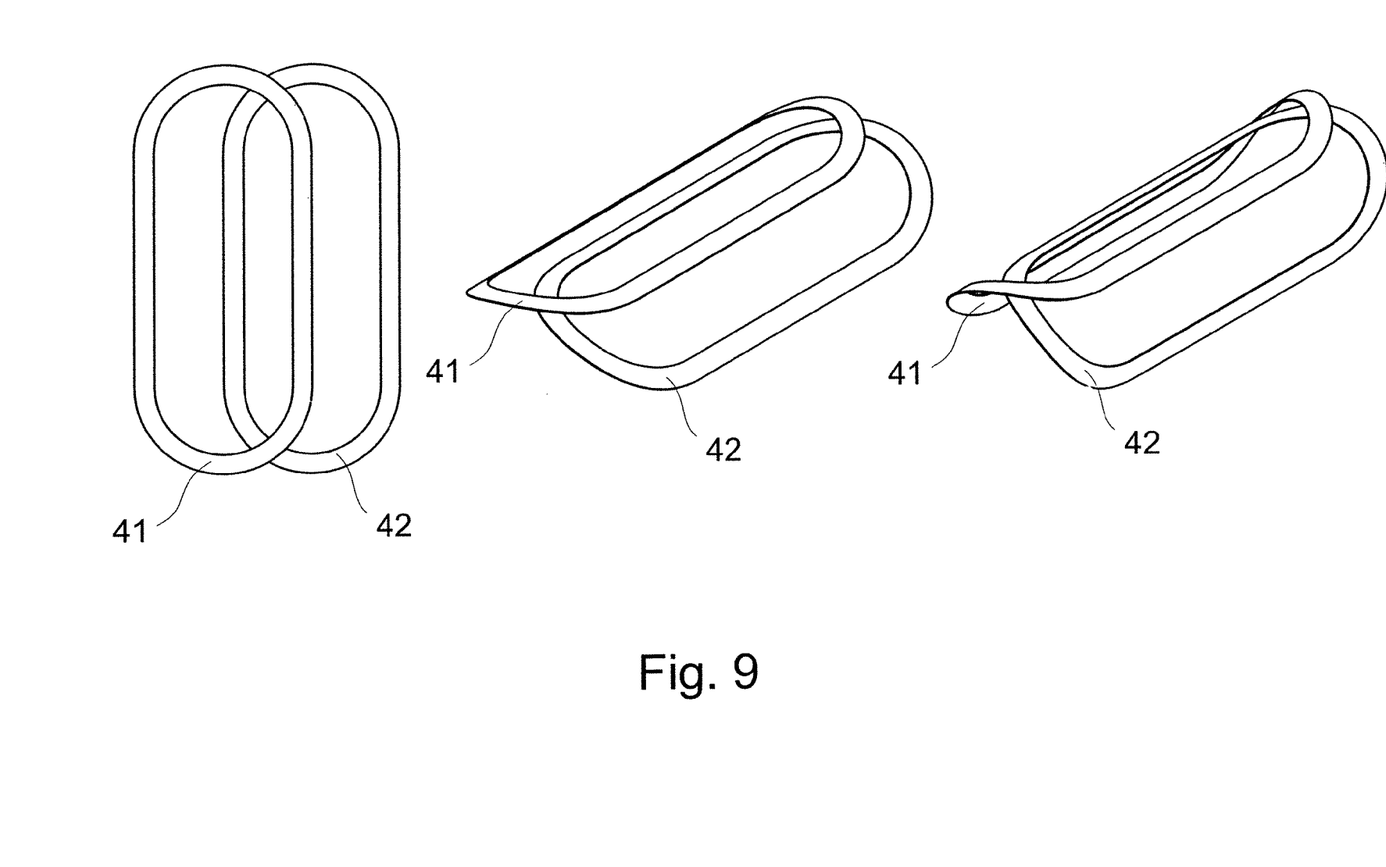
FIG. 9 Coils from right to left in the resting state of the rectal coil, in the bent-open state of the rectal coil and in the state of manufacture of the coil.

For a more accurate understanding, FIG. 9 typically shows the coils 41, 42, specifically such that they are overlapping one another. From right to left, the coils 41, 42 can be seen in the resting state of the rectal coil and simultaneously the state of manufacture of the half-tube 1, in the bent-open state of the rectal coil and thereby of the half-tube 1, and flat in the state of manufacture of the coil and of the flexible circuit board.

The coils 41, 42, can be positioned in the intestine not only by folding open the rectal coil, but also by means of a scissor mechanism, which is attached outside the fixture. The balloon 3 can, depending on the deployment, be used disposably, that is to say for once-only use, or, by means of an exchangeable protection, be repeatedly used.

In the plane of symmetry of the rectal coil and in the center of the coils 41, 42, there is an insertion means 51 for a puncture device. Centrally in the shaft 2 is located an opening 54 for introducing a guide slide 52. The guide slide 52 is inserted into the opening 54 and is connected to a rigidly formed or slightly flexible pipe 53. This can be displaced with the guide slide 52. For improved hygiene, a disposable product can be used for this purpose. The puncture device is introduced through the pipe 53, which thereby serves as a needle guide.

The pipe 53 can also be executed as an adequately rigid tube.

For calculation of the coordinates, a marker 55 is attached on the guide slide 52, auxiliary lines 56 on the shaft 2, so that calculation of the position of the lesion to be biopsied is possible. With the aid of the pipe 53, the displacement of the puncture device in the direction of the head or foot can be adjusted. The orientation of the puncture device, to the right or left, based on the body of the patient, can be achieved by rotating the tube 53 in the guide slide 52 or by a reorientation of the rectal coil, the latter, for example, by individual filling of the balloon chambers 31, 32. The depth is determined by measuring the distance between the lesion and marker 55. By displacing the guide slide 52 and the orientation of the rectal coil according to the invention, a targeted puncturing is achieved, which is not the case with the conventional rectal coil of the prior art.

The rectal coil according to the invention can develop its advantages even better if it is combined with a wedge-pillow. The use of the rectal coil and of the wedge-pillow is shown in FIG. 10. The patient 60 lies with his back on a base plate 61, which has thigh-support pillows 62 for the patient 60.

The buttocks and the pelvis lie on a coil construction 63, which can consist of one or more individual coils, in the latter case, for example a Siemens 6Ch Flex Coil. The coil construction can be laid in a tray at a first point 64. According to the invention, at at least one of the two sides of the patient's 60 body, it is inserted below the coil construction 63, that is to say, at the further point 65, a wedge-pillow is inserted, which, with the sharp end of the wedge, points in the direction of the backbone of the patient 60 or plane of symmetry of the base plate 61. The wedge pillow surfaces for support and for the slightly raised oblique position of the pelvis. The coil construction 63 is thereby also oriented or can be easily oriented so that the medium to be examined, in general the prostate, is always in focus and the coil construction 63 always has the optimum distance. The biopsy may be performed by means of a device 66, transrectally through the intestine between or next to the bent-open rectal coil, but also transperineally through the skin at the perineum between the anus and scrotum.

The wedge pillow is advantageously executed as part of a trough-shaped seat cushion. The seat cushion serves for raising the buttocks to ensure better transperineal or transrectal access. Likewise the coil construction 63, which contains the conventional flexible coils, can be part of the trough-shaped seat cushion or a support lying thereon. The coil construction 63 can be oriented onto the medium, in general the prostate, by means of the wedge cushion or the trough-shaped seat cushion or by means of an adjustment means. For the same purpose, a mechanism, for example with pneumatic or motor adjustment means, may be provided. Beneath the stomach of the patient 60 there is a construction 67, which is fixed by means of a strap, with at least one individual coil, which is usually also placed around the scrotum and penis of the patient 60.

In a similar manner, namely with the assistance of wedge pillows, body parts other than the prostate can also be examined.

The invention claimed is:

1. A rectal device for magnetic-resonance tomography comprising:
    at least one coil for transmitting and/or receiving electromagnetic signals of magnetic-resonance tomography;
    an inflatable balloon for fixing or positioning the coil in an intestine of a patent; and
    a shaft, with which the at least one coil and the balloon are connected and which serves for introducing the at least one coil into a rectum of the patient, wherein the entirety of each of the at least one coil is attached outside the balloon;
    wherein the at least one coil is attached in or on a half-tube having a semi-circular cross-sectional shape, which is designed so as to be flexible, and wherein the balloon is attached on the inside of the half-tube.

2. The rectal device according to claim 1, wherein the balloon is subdivided into a plurality of balloon chambers, which can be individually and separately subjected to air or liquid or gel.

3. The rectal device according to claim 2, wherein the balloon chambers are arranged in a longitudinal direction of the shaft, and are arranged side by side in the azimuth.

4. The rectal device according to claim 1, wherein the at least one coil is part of a flexible circuit board.

5. The rectal device according to claim 1, wherein the at least one coil comprises a plurality of coils for transmitting and/or receiving electromagnetic signals of magnetic-resonance tomography.

6. The rectal device according to claim 1, wherein additional devices are attached between the balloon and the at least one coil.

7. A method of performing magnetic-resonance tomography on a patient using the rectal device according to claim 1 comprising:
    inserting the at least one coil and the balloon into a rectum of the patient, wherein the at least one coil is in a closed state;
    inflating the balloon with liquid or gas;
    bending the at least one coil open in response to inflating the balloon; and
    performing magnetic-resonance tomography on the patient using the at least one coil.

8. The method according to claim 7, wherein inserting the at least one coil and the balloon into the rectum of the patient comprises inserting the at least one coil into an intestine of the patient in an axial direction in a defined length using a guide slide.

9. The method according to claim 7, further comprising inserting a wedge pillow below a pair of buttocks of the patient.

* * * * *